(12) United States Patent
Foley et al.

(10) Patent No.: US 11,820,865 B2
(45) Date of Patent: Nov. 21, 2023

(54) VICINAL DIOL ETHER DERIVATIVES OF POLYETHER POLYMERS

(71) Applicant: P2 Science, Inc., Woodbridge, CT (US)

(72) Inventors: Patrick Foley, New Haven, CT (US); Ashoke Bhattacharjee, Cheshire, CT (US); Tania Salam, Wallingford, CT (US); Matthew Alan Garcia, East Hartford, CT (US)

(73) Assignee: P2 SCIENCE, INC., Woodbridge, CT (US)

( * ) Notice: Subject to any disclaimer, the term of this patent is extended or adjusted under 35 U.S.C. 154(b) by 0 days.

(21) Appl. No.: 17/758,855

(22) PCT Filed: Jan. 14, 2021

(86) PCT No.: PCT/US2021/013486
§ 371 (c)(1),
(2) Date: Jul. 14, 2022

(87) PCT Pub. No.: WO2021/146461
PCT Pub. Date: Jul. 22, 2021

(65) Prior Publication Data
US 2023/0063141 A1  Mar. 2, 2023

Related U.S. Application Data

(60) Provisional application No. 63/125,842, filed on Dec. 15, 2020, provisional application No. 63/092,407, filed on Oct. 15, 2020, provisional application No. 63/043,251, filed on Jun. 24, 2020, provisional application No. 62/961,035, filed on Jan. 14, 2020.

(51) Int. Cl.
*C08G 65/00*  (2006.01)
*C08G 65/34*  (2006.01)
*C08G 65/26*  (2006.01)
*C08G 65/48*  (2006.01)

(52) U.S. Cl.
CPC .......... *C08G 65/48* (2013.01); *C08G 65/002* (2013.01); *C08G 65/34* (2013.01); *C08G 2650/64* (2013.01)

(58) Field of Classification Search
None
See application file for complete search history.

(56) References Cited

U.S. PATENT DOCUMENTS 9,982,073 B2   5/2018  Ghandi et al.
2006/0222723 A1 * 10/2006  Bevilacqua ............ A61P 25/22
                                                                424/769
2013/0202543 A1  8/2013  Kuper et al.
2017/0283553 A1 10/2017  Foley et al.

FOREIGN PATENT DOCUMENTS

EP         2842607       *  3/2015
WO    WO 2011/051945 A1 *  5/2011
WO    WO 2019/028053 A1     2/2019
WO    WO 2019/029808 A1     2/2019

OTHER PUBLICATIONS

Structure search by STIC, 10 pages, Mar. 1, 2023.*

* cited by examiner

*Primary Examiner* — Tae H Yoon
(74) *Attorney, Agent, or Firm* — Hoxie & Associates LLC

(57) ABSTRACT

The invention relates to vicinal diol ether derivatives of certain polyether polymers, compositions comprising the same, and methods of making the same via reaction with substituted or unsubstituted epoxides, and methods of using the same.

20 Claims, 1 Drawing Sheet

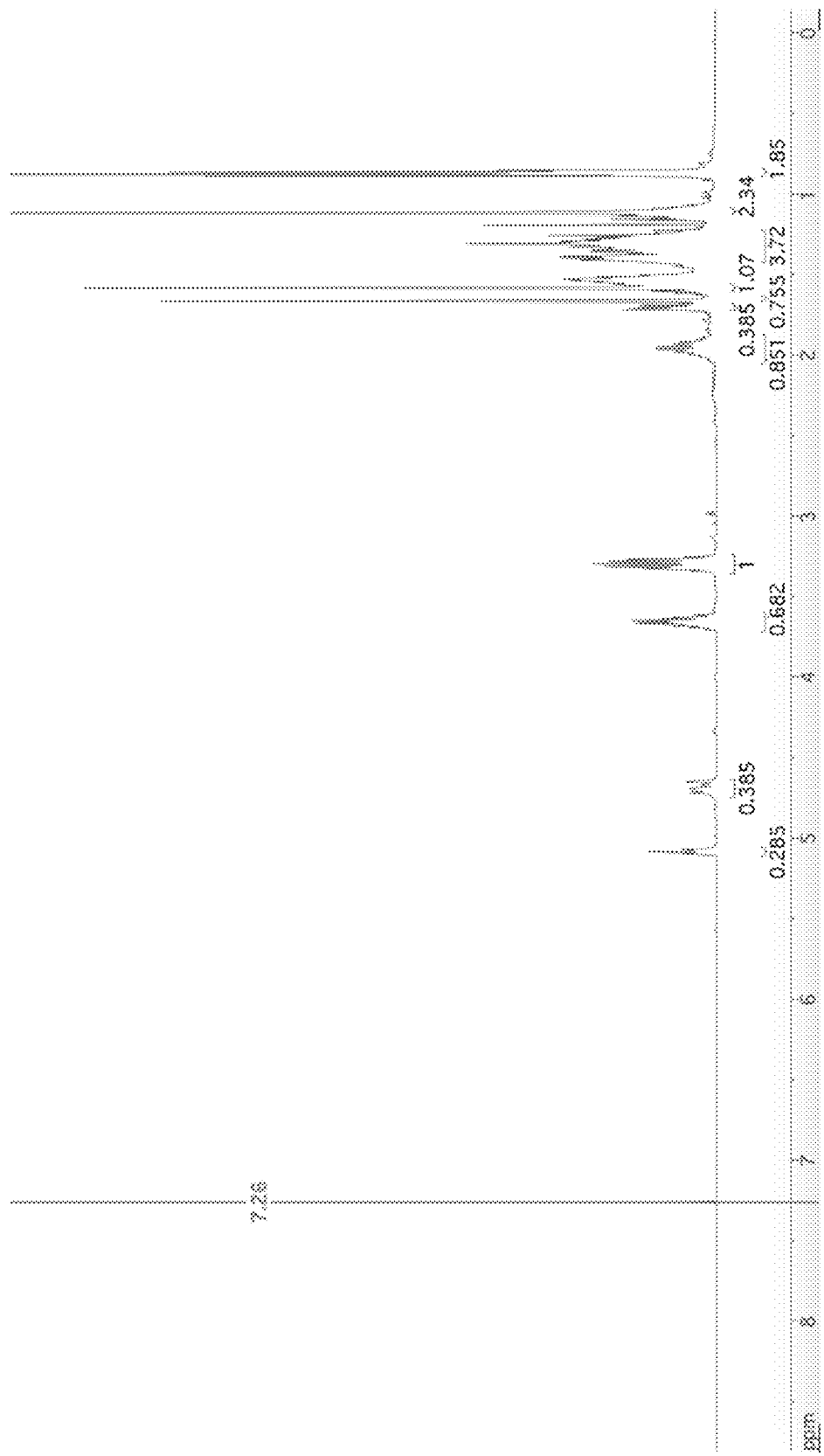

VICINAL DIOL ETHER DERIVATIVES OF POLYETHER POLYMERS

This application is a national stage entry under 35 U.S.C. § 371 of international PCT application No. PCT/US2021/013486, filed on Jan. 14, 2021, which claims priority to, and the benefit of, U.S. Provisional Applications 62/961,035, filed on Jan. 14, 2020, 63/043,251, filed on Jun. 24, 2020, 63/092,407, filed on Oct. 15, 2020, and 63/125,842, filed on Dec. 15, 2020, the contents of each of which are hereby incorporated by reference in their entireties.

FIELD

The invention relates to vicinal diol ether derivatives of certain polyether polymers, and methods of making the same via reaction with substituted or unsubstituted epoxides, compositions comprising the same, and methods of using the same. The polyether polymers precursors of said derivatives include, for example, polycitronellol, polyprenol, polyisocitronellol and polyisoprenol. The epoxides include straight-chain and branched-chain alkane and cycloalkane epoxides, including terpene epoxides.

BACKGROUND

Liquid polymers have important utility in cosmetic and personal care applications and play critical roles in visual displays, rheology, tribology, and drug delivery. For example, they can be used as lubricants, emollients, or as protective barriers for skin healing and UV protection. Ideally, these materials can be produced in a facile manner, be easily derivatized to modify function, and even more preferably be made from safe and sustainable raw materials.

Citronellol, prenol, and isoprenol are all naturally occurring molecules that are also commercially available on a large scale. However, these molecules possess an under-utilized combination of functionalities that allow them to be polymerized and functionalized: an isobutylenic group and an alcohol.

This type of chemistry has been mostly neglected in polymer chemistry. One reason for this could be due to the fact that the polymerization is an equilibrium reaction, and that readily abundant isobutylenic alcohols have not always been available. In recent years, however, the production of citronellol has been increasing rapidly, and one of the largest production routes also uses prenol and isoprenol as intermediates, thereby greatly increasing availability.

WO 2019/028053 discloses novel polymers derived from the naturally occurring and commercially available monomers citronellol, prenol and isoprenol. These monomers were effectively polymerized in a controlled way to yield a number of well-characterized polymeric ether alcohols. In addition, as these polymers as initially formed possess primary alcohol functional groups, WO 2019/028053 further discloses functionalization of the alcohol to derive various ether, ester and other derivative products.

BRIEF SUMMARY

In a surprising advancement in polymer science, the inventors' prior publications US 2017/0283553, US2017/0057940, and WO2019/028053, the contents of each of which are incorporated herein by reference, have taught generally how to prepare polyether polymers and derivatives thereof. These polyethers represent an advance in liquid polymer technology and carry with them many desirable benefits for commercial fields of application. Polyether polymers, and simple ether and ester derivatives thereof, have found use as lubricants, emollients, humectants, and surfactants.

The present disclosure builds on the inventors' prior work by providing new compounds, compositions, and methods for making such polymer derivatives with different physical and chemical properties. These structurally unique vicinal diol fragments are capable of modifying the properties of the polyether polymers to provide for a variety of new applications.

The polymer derivatives disclosed herein may be used in cosmetic or specialty chemical formulations and in some instances may be used as naturally derived alternatives to silicone polymers. These polymers can be formulated into various specialty chemical applications, including personal care compositions, in order to alter and improve the function of the product or application performance. The precise functionality of these polymers depends, however, on their size and composition, and hence both on their monomeric distribution, polydispersity, and any further functionalization.

Preferably, commercially available renewable terpene oxides (epoxides) such as limonene oxide, pinene oxide, styrene oxide, caryophyllene oxide, eugenol oxide, safrole oxide, myrcene oxide, carene oxide, menthene oxide are used in the present disclosure. Alternatively, epoxides such as ethylene oxide, propylene oxide, styrene oxide and cyclohexane oxide may be used.

In a first aspect, the present disclosure provides a compound according to Formula I below:

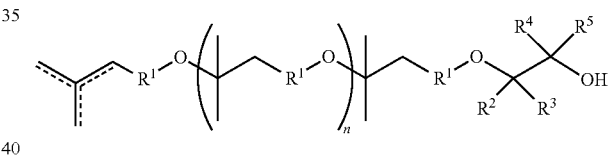

wherein $R^1$ is optionally substituted $C_1$-$C_{12}$ alkyl;

$R^2$, $R^3$, $R^4$, and $R^5$ are each independently hydrogen, optionally substituted $C_1$-$C_{12}$ alkyl, optionally substituted $C_2$-$C_{12}$ alkenyl, optionally substituted $C_2$-$C_{12}$ alkynyl, optionally substituted aryl (e.g., phenyl), or $R^2$ and $R^3$, $R^4$ and $R^5$, or $R^3$ and $R^5$, are taken together to form an optionally substituted $C_3$-$C_{12}$ cycloalkyl or optionally substituted $C_3$-$C_{12}$ cycloalkenyl; and n is an integer between 0 and 20 (e.g., 0-5).

It is understood that ===== represents an optional double bond (i.e., either a single or double bond), and thus that the terminal group,

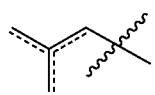

may have any one of the three indicated optional bonds present (i.e., a double bond) or all optional bonds absent (i.e., all single bonds).

In further aspects, the present disclosure provides further compositions, and methods of manufacturing said compounds and methods of using said compounds.

BRIEF DESCRIPTION OF THE DRAWINGS

FIG. 1 shows the $^1$H-NMR spectrum of the product of Example 2, taken in $CDCl_3$ solvent.

DETAILED DESCRIPTION

Without wishing to be bound by theory, isobutylenic groups can form ethers with alcohols through an acid catalyzed mechanism. This chemistry has been used in other instances to make ether bonds in organic synthesis.

The equilibrium nature of this reaction can potentially make it challenging to produce these ethers on a large scale. However, the inventors have discovered that with monomer recycling, proper catalyst selection, and highly concentrated reaction conditions, these molecules can reach sufficient degrees of polymerization in order to be used in a number of different applications. Further, these low molecular weight polymers can be further derivatized to reach much higher molecular weights and to achieve new functionality.

In a first aspect, the present disclosure provides a compound (Compound 1) according to Formula I below:

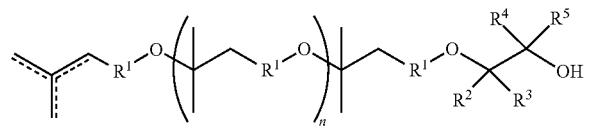

wherein $R^1$ is optionally substituted $C_1$-$C_{12}$ alkyl;

$R^2$, $R^3$, $R^4$, and $R^5$ are each independently hydrogen, optionally substituted $C_1$-$C_{12}$ alkyl, optionally substituted $C_2$-$C_{12}$ alkenyl, optionally substituted $C_2$-$C_{12}$ alkynyl, optionally substituted aryl (e.g., phenyl), or $R^2$ and $R^3$, $R^4$ and $R^5$, or $R^3$ and $R^5$, are taken together to form an optionally substituted $C_3$-$C_{12}$ cycloalkyl or optionally substituted $C_3$-$C_{12}$ cycloalkenyl; and n is an integer between 0 and 20 (e.g., 0-5).

In further embodiments of the first aspect, the disclosure provides any of the following:

1.1 Compound 1, wherein $R^1$ is optionally substituted linear $C_1$-$C_{12}$ alkyl or optionally substituted branched $C_1$-$C_{12}$ alkyl.
1.2 Compound 1, wherein $R^1$ is unsubstituted linear $C_1$-$C_{12}$ alkyl or unsubstituted branched $C_3$-$C_{12}$ alkyl.
1.3 Compound 1, wherein $R^1$ is unsubstituted linear $C_1$-$C_{12}$ alkyl.
1.4 Compound 1, wherein $R^1$ is unsubstituted branched $C_3$-$C_{12}$ alkyl.
1.5 Compound 1, wherein $R^1$ is $CH_2$.
1.6 Compound 1, wherein $R^1$ is unsubstituted branched or linear $C_6$ alkyl.
1.7 Compound 1, wherein $R^1$ is $CH_2CH_2CH(CH_3)CH_2CH_2$.
1.8 Compound 1 or any of 1.1-1.7, wherein one or more of $R^2$, $R^3$, $R^4$, and $R^5$ are each independently hydrogen.
1.9 Compound 1 or any of 1.1-1.7, wherein one or more of $R^2$, $R^3$, $R^4$, and $R^5$ are each independently unsubstituted $C_{1-12}$ alkyl (e.g., lower alkyl (e.g., $C_{1-6}$ alkyl).
1.10 Compound 1 or any of 1.1-1.7, wherein one or more of $R^2$, $R^3$, $R^4$, and $R^5$ are each independently selected from methyl, ethyl, propyl, isopropyl, n-butyl, isobutyl, sec-butyl, tert-butyl, n-pentyl, n-hexyl, n-octyl, or n-decyl.
1.11 Compound 1 or any of 1.1-1.7, wherein one or more of $R^2$, $R^3$, $R^4$, and $R^5$ are each independently substituted $C_{1-12}$ alkyl (e.g., $C_{1-6}$ alkyl substituted by 1-9 groups each independently selected from $C_{1-6}$ alkyl, $C_{1-6}$alkoxy, $C_{2-6}$alkenyl, $C_{2-6}$alkynyl, hydroxy, carboxy, halogen, and substituted or unsubstituted aryl).
1.12 Compound 1.11, wherein one or more of $R^2$, $R^3$, $R^4$, and $R^5$ are each independently $C_{1-6}$ alkyl (e.g., $C_{1-2}$ alkyl) substituted by 1-9 groups each independently selected from $C_{1-6}$ alkyl, $C_{1-6}$alkoxy, $C_{2-6}$alkenyl, $C_{2-6}$alkynyl, hydroxy, carboxy, halogen, and substituted or unsubstituted aryl.
1.13 Compound 1.12, wherein said aryl is optionally substituted by 1-4 groups each independently selected from $C_{1-6}$ alkyl, $C_{1-6}$alkoxy, $C_{2-6}$alkenyl, $C_{2-6}$alkynyl, hydroxy, carboxy, and halogen.
1.14 Compound 1.12, wherein said aryl is phenyl.
1.15 Compound 1.12, wherein said aryl is 3,4-methylenedioxyphenyl.
1.16 Compound 1.12, wherein said aryl is 3-hydroxy-5-methoxyphenyl.
1.17 Compound 1 or any of 1.1-1.7, wherein one or more of $R^2$, $R^3$, $R^4$, and $R^5$ are each independently unsubstituted $C_{2-12}$ alkenyl (e.g., $C_{3-9}$alkenyl).
1.18 Compound 1 or any of 1.1-1.7, wherein one or more of $R^2$, $R^3$, $R^4$, and $R^5$ are each independently substituted $C_{2-12}$ alkenyl (e.g., $C_{3-9}$alkenyl substituted by 1-9 groups each independently selected from $C_{1-6}$ alkyl, $C_{1-6}$alkoxy, $C_{2-6}$alkenyl, $C_{2-6}$alkynyl, hydroxy, carboxy, halogen, and substituted or unsubstituted aryl).
1.19 Compound 1.18, wherein one or more of $R^2$, $R^3$, $R^4$, and $R^5$ are each independently $C_{3-9}$alkenyl substituted by 1-4 groups each independently selected from $C_{1-6}$ alkyl, $C_{1-6}$alkoxy, $C_{2-6}$alkenyl, $C_{2-6}$alkynyl, hydroxy, carboxy, halogen, and substituted or unsubstituted aryl.
1.20 Compound 1.19, wherein one or more of $R^2$, $R^3$, $R^4$, and $R^5$ are each independently $C_{3-9}$alkenyl substituted by 1-4 groups each independently selected from $C_1$ 6 alkyl, $C_{1-6}$alkoxy, and $C_{2-6}$alkenyl, e.g., $C_{2-4}$alkenyl substituted by $C_{2-3}$alkenyl.
1.21 Compound 1 or any of 1.1-1.7, wherein one or more of $R^2$, $R^3$, $R^4$, and $R^5$ are each independently unsubstituted aryl (e.g., phenyl).
1.22 Compound 1 or any of 1.1-1.7, wherein one or more of $R^2$, $R^3$, $R^4$, and $R^5$ are each independently substituted aryl (e.g., phenyl substituted by 1-4 groups each independently selected from $C_{1-6}$ alkyl, $C_{1-6}$alkoxy, $C_{2-6}$alkenyl, $C_{2-6}$alkynyl, hydroxy, carboxy, and halogen).
1.23 Compound 1 or any of 1.1-1.7, wherein $R^2$ and $R^4$ are each independently hydrogen or unsubstituted $C_{1-6}$ alkyl (e.g., $C_{1-6}$ alkyl) and $R^3$ and $R^5$ are taken together to form an optionally substituted $C_3$-$C_{12}$ cycloalkyl or optionally substituted $C_3$-$C_{12}$ cycloalkenyl (e.g., optionally substituted by 1-9 groups independently selected from $C_1$-$C_{12}$ alkyl, $C_2$-$C_{12}$alkenyl, $C_2$-$C_{12}$alkynyl, $C_{1-6}$alkoxy, hydroxy, carboxy, or methylene (=$CH_2$)).
1.24 Compound 1.23, wherein $R^2$ and $R^4$ are each independently hydrogen or methyl.
1.25 Compound 1.23 or 1.24, wherein $R^3$ and $R^5$ are taken together to form a $C_6$-$C_{12}$ cycloalkyl optionally substituted by 1-6 groups, independently selected from $C_1$-$C_6$ alkyl, $C_2$-$C_6$alkenyl, and methylene (=$CH_2$)).
1.26 Compound 1.25, wherein $R^3$ and $R^5$ are taken together to form a $C_6$-$C_{12}$ cycloalkyl optionally substituted by 1-3 groups, independently selected from methyl, ethyl, isopropyl, vinyl, allyl, and methylene (=$CH_2$)).

1.27 Any one of Compounds 1.23-1.26, wherein said $C_3$-$C_{12}$ cycloalkyl (e.g., $C_6$-$C_{10}$ cycloalkyl) or $C_3$-$C_{12}$ cycloalkenyl is a bicyclic cycloalkyl or bicyclic cycloalkenyl.

1.28 Compound 1.27, wherein said $C_3$-$C_{12}$ cycloalkyl is a bicyclic $C_{6-9}$ cycloalkyl (e.g., a [4.1.0]heptane or [3.1.1]heptane bicyclic).

1.29 Compound 1.27, wherein said $C_3$-$C_{12}$ cycloalkyl is a bicyclic $C_{8-12}$ cycloalkyl (e.g., a [7.2.0]undecane bicyclic).

1.30 Compound 1 or any of 1.1 et seq., wherein n is 0 to 8.

1.31 Compound 1 or any of 1.1 et seq., wherein n is 0 to 6.

1.32 Compound 1 or any of 1.1 et seq., wherein n is 0 to 4.

1.33 Compound 1 or any of 1.1 et seq., wherein n is 0, 1, 2, 3, or 4.

1.34 Compound 1 or any of 1.1 et seq., wherein n is 0, 1 or 2.

1.35 Compound 1 or any of 1.1 et seq., wherein $R^1$ is $CH_2CH_2CH(CH_3)CH_2CH_2$, n is 0-3 (e.g., 0, 1 or 2).

1.36 Compound 1 or any of 1.1 et seq., wherein the terminal group is

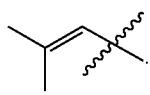

1.37 Compound 1 or any of 1.1 et seq., wherein the terminal group

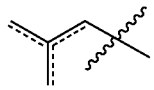

is

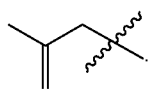

1.38 Compound 1 or any of 1.1 et seq., wherein the terminal group

is

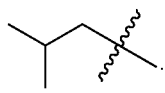

1.39 Compound 1 or any of 1.1 et seq., wherein the Compound of Formula I is:

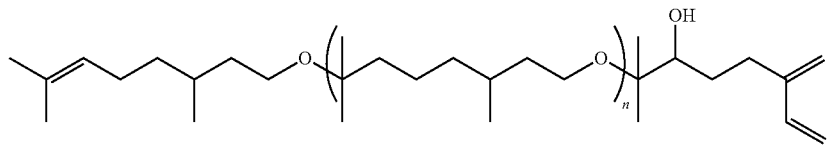

wherein n is 0-20 (e.g., 0, 1 or 2).

1.40 Compound 1 or any of 1.1 et seq., wherein the Compound of Formula I is:

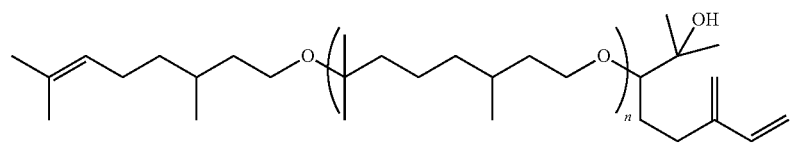

wherein n is 0-20 (e.g., 0, 1 or 2).

1.41 Compound 1 or any of 1.1 et seq., wherein the Compound of Formula I is:

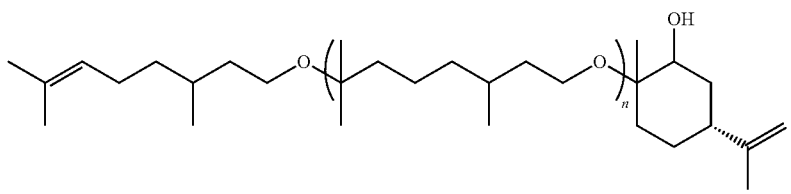

wherein n is 0-20 (e.g., 0, 1 or 2).

1.42 Compound 1 or any of 1.1 et seq., wherein the Compound of Formula I is:

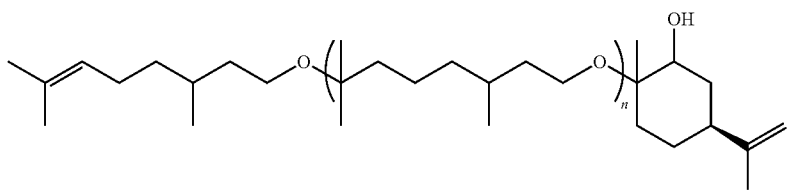

wherein n is 0-20 (e.g., 0, 1 or 2).

1.43 Compound 1 or any of 1.1 et seq., wherein the Compound of Formula I is:

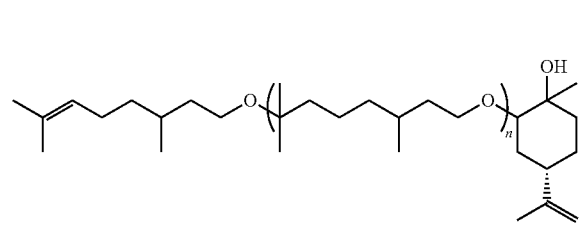

wherein n is 0-20 (e.g., 0, 1 or 2).

1.44 Compound 1 or any of 1.1 et seq., wherein the Compound of Formula I is:

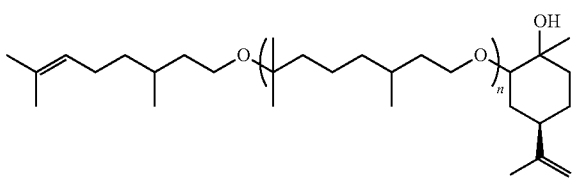

wherein n is 0-20 (e.g., 0, 1 or 2).

1.45 Compound 1 or any of 1.1 et seq., wherein the Compound of Formula I is:

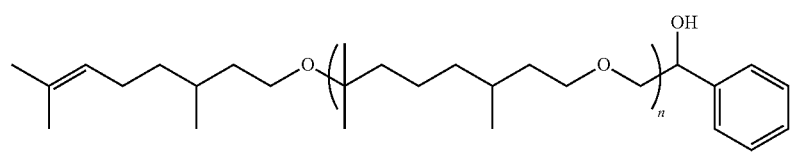

wherein n is 0-20 (e.g., 0, 1 or 2).

1.46 Compound 1 or any of 1.1 et seq., wherein the Compound of Formula I is:

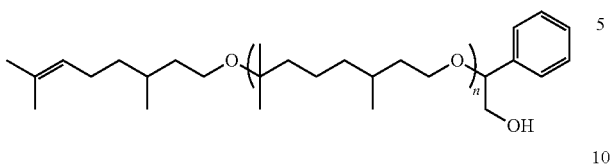

wherein n is 0-20 (e.g., 0, 1 or 2).

1.47 Compound 1 or any of 1.1 et seq., wherein the Compound of Formula I is:

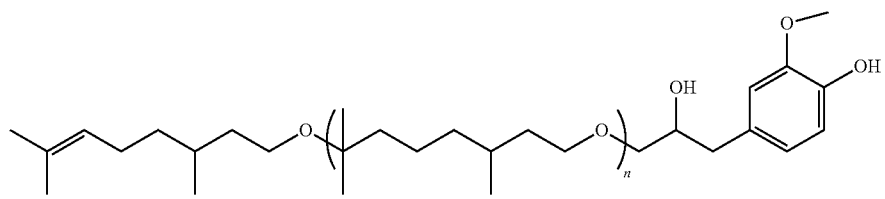

wherein n is 0-20 (e.g., 0, 1 or 2).

1.48 Compound 1 or any of 1.1 et seq., wherein the Compound of Formula I is:

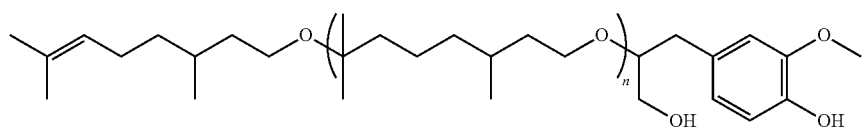

wherein n is 0-20 (e.g., 0, 1 or 2).

1.49 Compound 1 or any of 1.1 et seq., wherein the Compound of Formula I is:

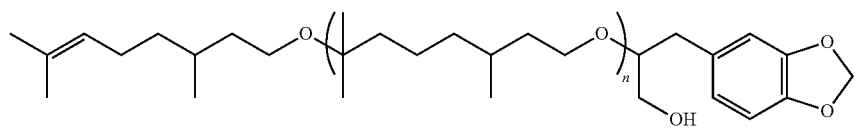

wherein n is 0-20 (e.g., 0, 1 or 2).

1.50 Compound 1 or any of 1.1 et seq., wherein the Compound of Formula I is:

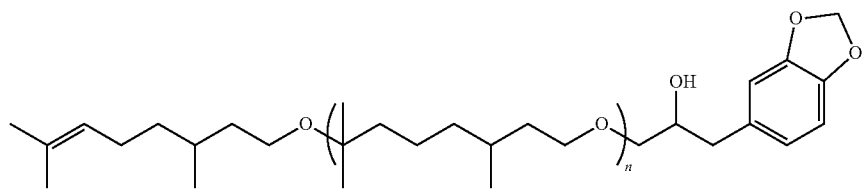

wherein n is 0-20 (e.g., 0, 1 or 2).

1.51 Compound 1 or any of 1.1 et seq., wherein the Compound of Formula I is:

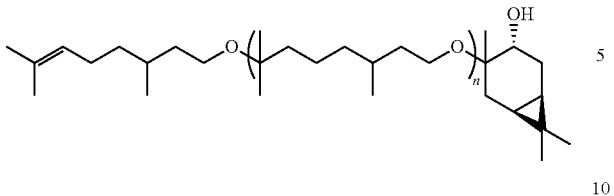

wherein n is 0-20 (e.g., 0, 1 or 2).

1.52 Compound 1 or any of 1.1 et seq., wherein the Compound of Formula I is:

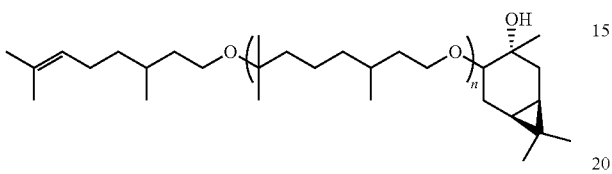

wherein n is 0-20 (e.g., 0, 1 or 2).

1.53 Compound 1 or any of 1.1 et seq., wherein the Compound of Formula I is:

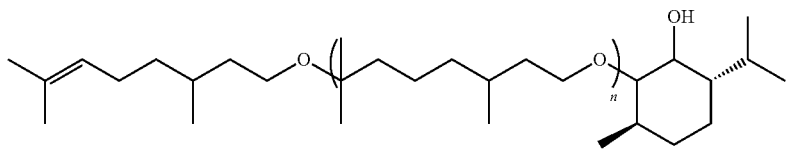

wherein n is 0-20 (e.g., 0, 1 or 2).

1.54 Compound 1 or any of 1.1 et seq., wherein the Compound of Formula I is:

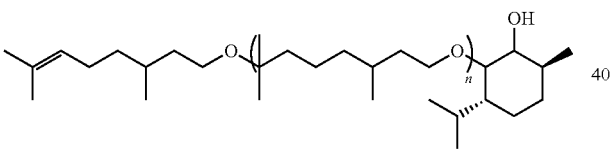

wherein n is 0-20 (e.g., 0, 1 or 2).

1.55 Compound 1 or any of 1.1 et seq., wherein the Compound of Formula I is:

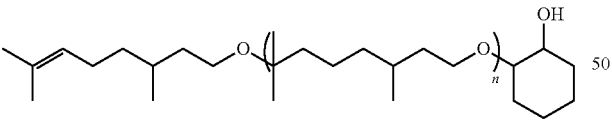

wherein n is 0-20 (e.g., 0, 1 or 2).

1.56 Compound 1 or any of 1.1 et seq., wherein the Compound of Formula I is:

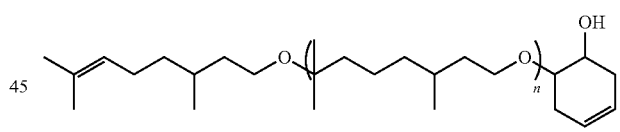

wherein n is 0-20 (e.g., 0, 1 or 2).

1.57 Compound 1 or any of 1.1 et seq., wherein the Compound of Formula I is:

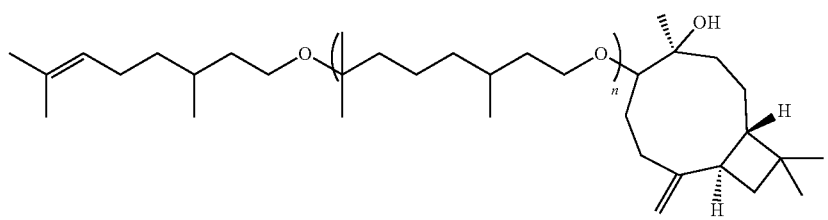

wherein n is 0-20 (e.g., 0, 1 or 2).

1.58 Compound 1 or any of 1.1 et seq., wherein the Compound of Formula I is:

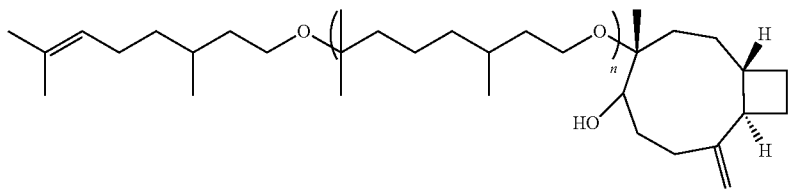

wherein n is 0-20 (e.g., 0, 1 or 2).

1.59 Compound 1 or any of 1.1 et seq., wherein the compound is enantiomerically enriched, e.g., having a diastereomeric excess (e.g., an enantiomeric excess (e.e.)) of greater than 70%.
1.60 Compound 1.59, wherein the compound has a diastereomeric excess (e.g., an enantiomeric excess (e.e.)) of greater than 80%, or greater than 85%, or greater than 90%, or greater than 95%, or greater than 97% or greater than 99%.
1.61 Compound 1.59 or 1.60, wherein each chiral carbon of the group $R^1$, has the (R)-configuration.
1.62 Compound 1.59 or 1.60, wherein each chiral carbon of the group $R^1$, has the (S)-configuration.

It is understood that the compounds of Formula I consist of a polymeric backbone that may be formed via a controlled homopolymerization reaction between monomeric units to form a compound of Formula I(a):

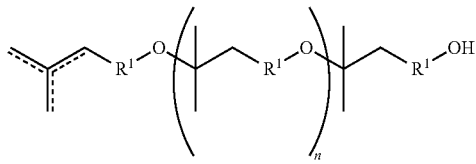

wherein n is 0-20 (e.g., 0, 1 or 2).

In some embodiments, the compound of Formula I(a) is the compound:

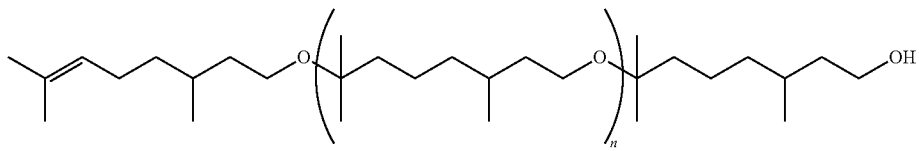

wherein n is 0-20 (e.g., 0, 1 or 2).

In a subsequent reaction (or more than one), the compound of Formula I may be formed by reacting the OH group of the compound of Formula I(a) with an epoxide of the Formula A:

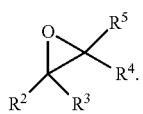

The resulting polymer derivative of Formula I will necessarily substantially retain the polymeric structural features—for example the values of n and the identities and structural relationships among and between the various monomeric units of the polymer backbone—from the corresponding compound of Formula I(a).

The polymerization reaction that forms the precursor compound of Formula I(a) necessarily will result in a mixture of products which vary in the value of the integer n, and as a result, also vary in the overall molecular weight of the polymer. This mixture of polymers may be difficult to completely purify, and moreover, it may be desirable to retain a mixture of polymers in order to take advantage of the unique physical and chemical properties which would inure to any mixture so formed. Thus, partial purification, by such means as distillation or chromatography, may be preferred to arrive at a mixture of related polymers having a certain set of desirable physical or chemical properties in the aggregate (e.g., boiling point, melting point, viscosity, surface tension, solubility, density, reactivity).

Therefore, in a second aspect, the present disclosure provides a Composition (Composition 2) comprising one or more compounds according to Formula I. In further embodiments of the second aspect, the present disclosure provides:

2.1 A composition comprising any one or more of Compound of 1.1-1.62.
2.2 A composition comprising one or more compounds each according to any one of compound 1.1-1.62, wherein said compounds differ only in their values of n.
2.3 A composition consisting of one or more compounds each according to any one of compound 1.1-1.62, wherein said compounds differ only in their values of n.
2.4 Composition 2 or any of 2.1-2.3, wherein the composition comprises a single compound according to any one of Compound 1 or 1.1-1.62, wherein the compound is present to an extent of greater than 40%, e.g., greater than 50%, greater than 60%, or greater than 70%, or greater than 80%, or greater than 90%, or 40-70% or 40-60%, or 40-50%, said percent being measured either as the number percent of the molecules in the composition or as the weight percent of the total weight of the composition.
2.5 Composition 2 or any of 2.1-2.4, wherein the composition comprises one or more compounds (e.g., from one up to ten specific compounds), wherein each compound is independently a compound according to Compound 1 or 1.1-1.62, each compound being present in an amount of at least 1% and up to 90%, e.g., 5 to 50%, or 5 to 40% or 5 to 30%, or 5 to 25%, or 5 to 20% or 5 to 15%, or 5 to 10%, or 40 to 50%, or 30 to 40% or 20 to 30%, or 10 to 20%, or 1 to 10%, or 1 to 5%, or 1 to 2%, said percent being measured either as the number percent of the molecules in the composition or as the weight percent of the total weight of the composition.

2.6 Composition 2, or any one of Compositions 2.1 to 2.5, wherein the number average molecular weight ($M_n$) of the compounds in the composition, optionally exclusive of the group —$(OCR^2R^3CR^4R^5)$—OH, is 150 to 2000 Daltons (e.g., 300 to 800 Daltons).

2.7 Composition 2.6, wherein the number average molecular weight ($M_n$) of the compounds in the composition, optionally exclusive of the group —$(OCR^2R^3CR^4R^5)$—OH, is 300 to 1900 Daltons, e.g., 300 to 1600 Daltons, or 300 to 1300 Daltons, or 300 to 1100 Daltons, or 300 to 1000 Daltons, or 300 to 800 Daltons, or 300 to 700 Daltons, or 300 to 500 Daltons, or 400 to 1000 Daltons, or 400 to 700 Daltons, or 600 to 1100 Daltons, or 600 to 1000 Daltons, or 600 to 800 Daltons or about 500 Daltons, or about 414 Daltons.

2.8 Composition 2, or any one of Compositions 2.1 to 2.7, wherein the weight average molecular weight ($M_w$) of the compounds in the composition, optionally exclusive of the group —$(OCR^2R^3CR^4R^5)$—OH, is 150 to 2000 Daltons.

2.9 Composition 2.8, wherein the weight average molecular weight ($M_w$) of the compounds in the composition, optionally exclusive of the group —$(OCR^2R^3CR^4R^5)$—OH, is 300 to 1900 Daltons, e.g., 300 to 1600 Daltons, or 300 to 1300 Daltons, or 300 to 1100 Daltons, or 300 to 1000 Daltons, or 300 to 800 Daltons, or 300 to 700 Daltons, or 300 to 500 Daltons, or 400 to 1000 Daltons, or 400 to 700 Daltons, or 600 to 1100 Daltons, or 600 to 1000 Daltons, or 600 to 800 Daltons, or about 438 Daltons.

2.10 Composition 2, or any one of Compositions 2.1 to 2.9, wherein the polydispersity ($M_w/M_n$) of the compounds in the composition (optionally without taking into account the mass of the group —$(OCR^2R^3CR^4R^5)$—OH) is in the range of 1 to 5.

2.11 Composition 2.10, wherein the polydispersity ($M_w/M_n$) is in the range of 1 to 4, or 1 to 3, or 1 to 2.5, or 1 to 2, or 1 to 1.5, or about 1 to 1.25, or about 1, or 1.5 to 3.5, or 1.5 to 2.5, or about 1.5, or 2 to 4, or 2 to 3, or 2 to 2.5, or about 2, or 1 to 1.25, or 1 to 1.20, or 1 to 1.15, or 1 to 1.10, or about 1.06.

2.12 Composition 2, or any one of Compositions 2.1 to 2.11, wherein the compounds in the composition have an average n value of 0 to 8, measured either as a weight average or number average.

2.13 Composition 2.12, wherein the compounds in the composition have an average n value of 0 to 6, measured either as a weight average or number average.

2.14 Composition 2.12, wherein the compounds in the composition have an average n value of 0 to 5, measured either as a weight average or number average.

2.15 Composition 2.12, wherein the compounds in the composition have an average n value of about 0, about 1, about 2, about 3, or about 4, measured either as a weight average or number average.

2.16 Composition 2.12, wherein the compounds in the composition have an average n value of about 0, about 1 or about 2, measured either as a weight average or number average.

2.17 Composition 1.62, wherein the compounds in the composition have an average n value of about 0.5, e.g., about 0.52, measured as the weight average.

2.18 Composition 1 or any of 1.1 et seq., wherein the compounds in the compositions are all

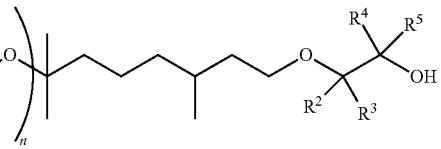

wherein $R^2$ is and n is from 0 to 8 (e.g., 0 to 4).

2.19 Composition 2.18, wherein at least 95% of the compounds by weight have an n value of 0, 1, 2 3 or 4, e.g., at least 97% or at least 98% or at least 99% of said compounds.

2.20 Composition 2.19, wherein at least 90% of the compounds by weight have an n value of 0, 1 or 2, e.g., 90-98% or 95-98% of said compounds.

2.21 Composition 2.20, wherein at least 70% of the compounds by weight have an n value of 0 or 1, e.g., at least 80%, or 80-90% or 80-85% of said compounds.

2.22 Composition 2.21, wherein at least 30% of the compounds by weight have an n value of 0, e.g., at least 40%, or 40-60% or 45-55% of said compounds.

It is understood that the compositions according to Composition 2 et seq., described herein, comprise a mixture of discrete polymers according to Formula I which vary in the precise value of the integer n (and optionally further comprising any other ingredients). Thus, the Composition 2 et seq. may be understood to be a mixture of compounds of Formula I having different values for the integer n, e.g., at least two different compounds of Formula I having different values for the integer n (for example, a mixture which comprises a compound of Formula I wherein n is 0, and a compound of Formula I wherein n is 1). Typically, in such compositions, substantially all polymers according to Formula I in the composition will have the same groups $R^1$, $R^2$, $R^3$, $R^4$, and $R^5$, that is, the various polymers according to Formula I in the composition will differ only in the value of the integer n. As used in the preceding sentence (and analogously elsewhere herein), the term "substantially all polymers according to Formula I" is understood to recognize that minor synthetic impurities may be present in which $R^1$, $R^2$, $R^3$, $R^4$, and/or $R^5$, differ from that of the bulk of the composition (e.g., owing to minor impurities in starting materials, minor side-products in the synthesis, or minor amounts of unreacted intermediates, which may be present despite efforts at purification). In particular embodiments, the Composition 2 et seq. may comprise a mixture of compounds of Formula I having values of n selected from one or more of 0, 1, 2, 3, 4, 5, 6 and 7.

It is understood that FIGURES for average molecular weight and polydispersity for Compounds of Formula (I) may be described based on the polymer backbone of the molecule, i.e., the portion corresponding to the Formula I(a), less the hydroxyl hydrogen. For example, measurements and calculations of molecular weight and polydispersity can be made on the alcoholic polymer (Formula I(a)) prior to reaction with the epoxide compound, and the resulting values can be extrapolated to the later-derived derivatives of Formula I.

In a third aspect, the present disclosure provides a method (Method 3) of making a compound of Formula I, the method comprising the step of reacting a compound of Formula I(a) with a compound of Formula A in the presence of an acid or base catalyst, followed by isolation and complete or partial purification of the compound of Formula I (e.g., by distillation or chromatography).

In further embodiments of the third aspect, the disclosure provides any of the following:
- 3.1 Method 3, wherein the product of the method is a compound of Formula I, or of any of 1.1-1.62.
- 3.2 Method 3, wherein the product of the method is Composition 2, or any of 2.1-2.22.
- 3.3 Method 3, 3.1 or 3.2, wherein the catalyst is an acid catalyst (e.g., an acidic ion exchange resin).
- 3.4 Method 3.3, wherein the acid catalyst is a resin functionalized with carboxylic acid or sulfonic acid moieties e.g., Amberlyst-type resin (a macroreticular or cellular resins or silica covalently bonded to sulfonic acid or carboxylic acid groups).
- 3.5 Method 3.3, wherein the acid catalyst is a neat acid or a soluble acid.
- 3.6 Method 3.5, wherein the acid is a Lewis acid, e.g., selected from ferric chloride, calcium chloride, titanium chloride, boron trifluoride, zinc trifluoromethanesulfonate, magnesium perchlorate, sodium perchlorate, and lithium perchlorate.
- 3.7 Method 3.5, wherein the acid is a Bronsted acid, e.g., selected from sulfuric acid, hydrochloric acid, hydrobromic acid, methanesulfonic acid, trifluoromethanesulfonic acid, acetic acid, toluenesulfonic acid, phosphoric acid, trifluoroacetic acid, trichloroacetic acid, perchloric acid, and formic acid.
- 3.8 Method 3.3, wherein the catalyst is a base catalyst (e.g., a hydroxide, carbonate, bicarbonate, alkoxide, or hydride).
- 3.9 Method 3.8, wherein the base is selected from a lithium, sodium, potassium, calcium or magnesium salt of hydroxide, carbonate, bicarbonate, methoxide, ethoxide, propoxide or hydride.
- 3.10 Any of Methods 3.3-3.9, wherein the catalyst is dissolved or suspended in a solvent, e.g., an organic solvent, aqueous solvent, or miscible mixture thereof, optionally with a phase-transfer agent.
- 3.11 Method 3.10, wherein the method comprises the step of combining the compound of Formula I(a) and the compound of Formula A in the solvent or mixture of solvents and then adding the catalyst to the resulting solution or suspension.
- 3.12 Method 3.10, wherein the method comprises the step of combining the compound of Formula I(a) and the compound of Formula A in the solvent or mixture of solvents and then passing the mixture through a fixed bed comprising the catalyst (e.g., wherein the catalyst is a resin-bound catalyst).
- 3.13 Any of Methods 3.3-3.9, wherein the catalyst is dissolved or suspended in the neat mixture of the compound of Formula I(a) and the compound of Formula A.
- 3.14 Method 3 or any of Methods 3.1-3.13, wherein the temperature of the reaction is from 30 and 120° C., e.g., from 40 and 60° C.
- 3.15 Method 3 or any of Methods 3.1-3.14, wherein the reaction occurs in a batch reactor.
- 3.16 Method 3 or any of Methods 3.1-3.14, wherein the reaction occurs in a continuous packed-bed reactor.
- 3.17 Method 3 or any of Methods 3.1-3.16, wherein the product is isolated by distillation, e.g., vacuum distillation.

The term "compounds of the present disclosure" and "compositions of the present disclosure" include, respectively, the compounds of Formula I and Compounds 1 and 1.1-1.62, and Compositions 2 and 2.1-2.22, and any and all other embodiments thereof.

In some embodiments of the present disclosure, the compounds and compositions of the present disclosure have a polyether backbone having a number average molar weight ($M_w$) of in the range of from 150-3000 g/mol, preferably in the range of from 00-500 g/mol, for example, as measured by means of isocratic chromatography using THF as a mobile phase in HPLC.

In some embodiments, the compositions of the present disclosure have a polydispersity ($M_w/M_n$) in the range of 1 to 5, and preferably 1 to 2. In some embodiments, the compounds of the present disclosure are based on a polyether alcohol derived from the homopolymerization product of citronellol, geraniol, linalool, citronellic acid, limonene, dihydromyrcene, myrcenol, adipic acid, propanediol, ethylene glycol, glycerol, 1,9-nonnanediol or 1,6-hexanediol. Preferably they are based on the polymerization of citronellol and derivatization thereof.

In some embodiments, the compositions of the present disclosure comprise compounds having number average molecular weight of polyether alcohol and derivatives thereof in the range of from 100-1000 g/mol, preferably in the range from 100-500 g/mol. Number average molecular weight may be measured by means of isocratic chromatography, such as, using Agilent Oligopore GPC column and THF as a mobile phase in HPLC.

Compounds and compositions of the present disclosure, especially those having a polydispersity of 1 to 2, have one or more of the following favorable features: the compounds are short-chain polymers; the compounds are made using a reversible polymerization reaction; the polymers are biodegradable and biocompatible; and the polymers may be manufactured using all-natural ingredients. These are important benefits in many of the commercial applications in which these compounds may be used. The compositions disclosed herein, with the polydispersity in the range of from 1 to 5, preferably 1 to 2, are suitable as replacement or substitutes for surfactants, polymers, and silicones in a variety of commercial products, such as in cosmetics and pharmaceutical compositions, and as adjuvants in crop care formulations, and as lubricants or solvents in enhanced oil recovery, fracking and oil field applications. The compounds and compositions disclosed herein offer improved physical characteristics, such as appearance, odor, viscosity, refractive index and/or surface tension.

In some embodiments, the compositions of the present disclosure comprise compounds having a weight average molecular weight ($M_w$) of equal to or greater than 100, 200, 300, 400, 500, 600, 700, 800, 900 and 1000 Daltons. In another embodiment, the weight average molecular weight may be selected from the group consisting of: 330, 331, 332, 333, 334, 335, 336, 337, 338, 339, 340, 341, 342, 343, 344, 345, 346, 347, 348, 349, 350, 351, 352, 353, 354, 355, 356, 357, 358, 359 and 360 Daltons.

In some embodiments of this invention, the polydispersity index (PDI) of the compounds and compositions of the disclosure is less than or about 1.25, 1.24, 1.23, 1.22, 1.21, 1.20, 1.19, 1.18, 1.17, 1.16, 1.15, 1.14, 1.13, 1.12, 1.11 or 1.10. In some embodiments, the PDI may be equal to or greater than 1.00, 1.01, 1.02, 1.03, 1.04, 1.05, 1.06, 1.07, 1.08 or 1.09.

In some embodiments of the present disclosure, the compounds and compositions disclosed herein are useful: for fragrance retention, fixation of fragrances, or as a fragrance carrier; as a malodor counteracting agent; in paints and coatings; as an adjuvant for crop control; as a cosmetic ingredient (e.g., as a silicone replacement or a white oil replacement); in nail polish; in writing or printing inks; as a resin or resin-replacement; as an insect repellant (e.g., a mosquito repellent); and in sun block formulations. The polymeric compounds with aforementioned properties can have one of the following average molecular weight ($M_w$) 390, 391, 392, 393, 394, 395, 396, 397, 398, 399, 400, 401, 402, 403, 404, 405, 406, 407, 408, 409, 410, 411, 412, 413, 414, 415, 416, 417, 418, 419 and 420 Daltons. In other embodiments the polymeric compounds with aforementioned properties can have polydispersity index (PDI), equal or greater than 1.00, 1.01, 1.02, 1.03, 1.04, 1.05, 1.06, 1.07, 1.08 and 1.09.

Methods to make the polyethers of Formula I(a) are described in US2017/0283553 and WO2019/028053, the contents of which are incorporated by reference herein in their entireties. Such polymers can generally be made with high degrees of polymerization in a short period of time by using a resin-bound acid catalyst, such as Amberlyst®, under neat, solvent-free conditions. Amberlyst-type resins are recognized in the art and understood to be macroreticular or cellular resin covalently bonded to sulfonic acid or carboxylic acid groups, preferably sulfonic acid groups. Such polymerizations can be done at or below room temperature, preferably at slightly elevated temperature, between 30 and 110° C., or even more preferably between 40 and 90° C. (e.g., about 50° C.). Such polymerizations can take place in batch reactors, semi-batch reactors, or even more preferably in continuous packed bed-type reactors of the type described in U.S. Provisional Application 62/384,939 and PCT/US2017/50808 and US 2019-0210948, the contents of each of which are incorporated herein by reference.

The reversibility of the polymerization of the claimed compounds derives from the nature of these polymers, having adjacent oxygen atoms and tertiary carbon atoms. As a result, under conditions which will promote the cleavage of the O—C bond, the resulting tertiary carbocation is unusually stable. This leads to facile abstraction of an adjacent hydrogen atom to regenerate the starting materials' alcohol and alkene functional groups. Such de-polymerization may be promoted by mildly acidic conditions (e.g., with Lewis acids or Brønsted acids) or by thermal conditions or by enzymatic conditions (as by enzymes found in naturally occurring bacteria).

This depolymerization property results in biodegradation. This property also permits the formation of compositions comprising the compounds wherein the depolymerization of the polymers may be controlled to permit slow release of the monomeric polymer constituents (e.g., citronellol) or of shortened polymeric constituents (e.g., the release of dimers of citronellol by depolymerization of a larger polymer). The present disclosure embraces solid and/or liquid formulations (e.g., products) comprising any of the compounds or composition described herein, such that the wherein the formulation provides for slow, controlled depolymerization of the polymers and diffusion of the resulting monomers and or shortened oligomers so that that can be released from the composition (e.g., by vaporization at the surface of the composition). Such formulations may be comprised of ingredients which accelerate such depolymerization (such as Lewis acids or Brønsted acids, or enzymes) or such formulations may be associated with a device comprising an electrical heating element to promote thermal depolymerization. The monomers and/or shortened oligomers produced in this manner (e.g., citronellol or dimers or trimers of citronellol) are themselves beneficial for any number of reasons, e.g., as fragrances, insect repellants, anti-oxidants, anti-microbials, or as active pharmaceutical ingredients (e.g., where the composition is a pharmaceutical composition).

The compounds and compositions disclosed herein are particularly suitable for the replacement of silicones, mineral oil and/or paraffins, in cosmetic compositions, such as concealers, primers and/or moisturizers.

In a fourth aspect, the present disclosure provides a product composition (Product 1), which product composition comprises a Compound 1 or any of 1.1-1.62, or a Composition 2 or any of 2.1-2.22, in combination with at least one suitable solvent, carrier, or other excipient. In further embodiments of the fourth aspect, the present disclosure provides product compositions as follows:

1.1 Product 1, wherein the product composition is a fragrance product composition.
1.2 Product 1, wherein the product composition is a perfume product composition.
1.3 Product 1, wherein the product composition is a soap product composition.
1.4 Product 1, wherein the product composition is an insect repellant product composition, for example, a mosquito repellant product composition.
1.5 Product 1, wherein the product composition is an insecticide product composition.
1.6 Product 1, wherein the product composition is a detergent product composition.
1.7 Product 1, wherein the product composition is a household cleaning agent product composition.
1.8 Product 1, wherein the product composition is an air freshener product composition.
1.9 Product 1, wherein the product composition is a room spray product composition.
1.10 Product 1, wherein the product composition is a pomander product composition.
1.11 Product 1, wherein the product composition is a candle product composition.
1.12 Product composition 1.11, wherein the product composition further comprises a paraffin wax and/or beeswax base.
1.13 Product composition 1.12, wherein the product composition consists of the Compound 1 or any of 1.1-1.62, or the Composition 2 or any of 2.1-2.22, dispersed within the paraffin wax and/or beeswax base, with a suitable wick embedded therein.

1.14 Product 1, wherein the product composition is a cosmetic product composition.
1.15 Product 1, wherein the product composition is a toilet water product composition.
1.16 Product 1, wherein the product composition is a pre- and aftershave lotion product composition.
1.17 Product 1, wherein the product composition is a talcum powder product composition.
1.18 Product 1, wherein the product composition is a haircare product composition.
1.19 Product 1, wherein the product composition is a body deodorant product composition.
1.20 Product 1, wherein the product composition is an anti-perspirant product composition.
1.21 Product 1, wherein the product composition is a shampoo product composition.
1.22 Product 1, wherein the product composition is a pet litter product composition.
1.23 Product 1, wherein the product composition is a topically applied skin care product composition, optionally wherein the skin care product is selected from skin-conditioning agents; skin penetration enhancing agents; skin protectants; skin soothing agents; shaving creams and shaving gels; skin creams and lotions (e.g., moisturizing creams and lotions); skin healing agents; ultraviolet light absorbers or scattering agents; sequestrants; anti-acne agents; anti-androgens; depilation agents; keratolytic agents/desquamation agents/exfoliants such as salicylic acid; panthenol moisturizer such as D-panthenol; soluble or colloidally-soluble moisturizing agents such as hyaluronic acid and starch-grafted sodium polyacrylates; and sunscreens.
1.24 Product composition 1.23, wherein the skin care product is a skin protectant.
1.25 Product composition 1.23, wherein the skin care product is a skin soothing agent.
1.26 Product composition 1.23, wherein the skin care product is a sunscreen.
1.27 Product 1, wherein the product composition is a paint or coating product composition.
1.28 Product 1, wherein the product composition is a lubricant product composition.
1.29 Product 1, wherein the product composition is a plastic product composition.
1.30 Product 1, wherein the product composition is a defoamer product composition.
1.31 Product 1, wherein the product composition is a hydraulic fluid product composition.
1.32 Product 1, wherein the product composition is an antimicrobial product composition.
1.33 Product 1, wherein the product composition is a crop care product composition, e.g., wherein said compound is an adjuvant in the crop care formulation.
1.34 Product 1, wherein the product composition is a product composition for enhanced oil recovery, fracking and/or other oil field applications, e.g., wherein said compound is lubricant or solvent in said formulation.
1.35 A product comprising any preceding composition wherein said composition is stored or housed in a receptacle comprising an electrical heating element, wherein actuation of the heating element results in heating of the composition, thermal decomposition of the Compound, and release of volatile substances.
1.36 A fragrance of perfume product comprising Compound 1 or any of 1.1-1.62, or a Composition 2 or any of 2.1-2.22, or any mixtures thereof, wherein said compound is used as a fragrance retention agent, a fragrance fixative or a fragrance carrier.
1.37 A cosmetic product comprising Compound 1 or any of 1.1-1.62, or a Composition 2 or any of 2.1-2.22, or any mixtures thereof, wherein said compound is used as a replacement for silicone and/or as a replacement for white oil.
1.38 A nail polish product comprising Compound 1 or any of 1.1-1.62, or a Composition 2 or any of 2.1-2.22, or any mixtures thereof.
1.39 A writing ink or printing ink product comprising Compound 1 or any of 1.1-1.62, or a Composition 2 or any of 2.1-2.22, or any mixtures thereof.
1.40 An adhesive product composition comprising Compound 1 or any of 1.1-1.62, or a Composition 2 or any of 2.1-2.22, or any mixtures thereof.
1.41 An oral care product composition comprising Compound 1 or any of 1.1-1.62, or a Composition 2 or any of 2.1-2.22, or any mixtures thereof; optionally wherein the oral care product composition is selected from a toothpaste, tooth gel, or mouthwash.
1.42 A food product composition comprising Compound 1 or any of 1.1-1.62, or a Composition 2 or any of 2.1-2.22, or any mixtures thereof; optionally wherein the food product composition is selected from a chewing gum or carbonate beverage.
1.43 A pharmaceutical product comprising Compound 1 or any of 1.1-1.62, or a Composition 2 or any of 2.1-2.22, or any mixtures thereof; optionally wherein the pharmaceutical product composition is selected from a capsule, a tablet (e.g., a chewable tablet), a syrup (e.g., a cough syrup), a lozenge (e.g., a cough drop), and a liquid (e.g., a solution or suspension for oral ingestion).
1.44 Any preceding Product composition, wherein the product composition is an aerosol product.
1.45 Product composition 1.44, wherein the product is an aerosol deodorant, aerosol anti-perspirant, aerosol body spray, aerosol air freshener, aerosol fragrance or perfume product, aerosol insecticide, aerosol lubricant, aerosol hair care product (e.g., hair spray), aerosol sunscreen, aerosol throat analgesic, or aerosol insect repellant.
1.46 Product 1.44 or 1.45 wherein the Product composition further comprises an aerosol propellant, e.g., propane, n-butane, isobutane, dimethyl ether, diethyl ether, methyl ethyl ether, chlorofluorocarbons, fluorocarbons, hydrochlorofluorocarbons, hydrofluorocarbons (e.g., 1,1-difluoroethane, or 1,1,1-trifluoroethane, or 1,1,1,2-tetrafluoroethane, or 1,1,1,3,3-pentafluoropropane, or 1,1,1,3,3-pentafluorobutane, or 1,1,1,2,3,3,3-heptafluoropropane, or 1,3,3,3-tetrafluoropropene, or 2,3,3,3-tetrafluoropropene), nitrous oxide, carbon dioxide, nitrogen, air or any combination thereof.
1.47 Any of Product compositions 1.44-1.46, wherein the product is an aerosol body spray, optionally comprising a propellant selected from propane, n-butane, isobutane, 1,1-difluoroethane, 1,1,1-trifluoroethane, 1,1,1,2-tetrafluoroethane, 1,1,1,3,3-pentafluoropropane, 1,1,1,3,3-pentafluorobutane, 1,1,1,2,3,3,3-heptafluoropropane, and a combination thereof, such as in particular, a combination of propane, n-butane, isobutane and 1,1-difluoroethane.

In another embodiment, the present disclosure provides a Compound 1 or any of 1.1-1.62, or a Composition 2 or any of 2.1-2.22, or any mixtures thereof, for use in Product Composition 1, or any of 1.1-1.47.

In other embodiments of the preceding aspects, the present disclosure provides a composition comprising Compound 1 or any of 1.1-1.62, or a Composition 2 or any of 2.1-2.22, or any mixtures thereof, or Product 1 or any of 1.1-1.47, wherein the composition or product further comprises one or more additives selected from: a cooling sensate, a warming sensate and/or a tingling sensate; a flavorant or fragrance; vitamins, minerals, nutraceuticals, energizing agents, soothing agents, coloring agents, amino acids antioxidants, preservatives, pH modifying agents, viscosity adjusting agents, and combinations of any preceding.

In particular embodiments, such compositions comprise a cooling, warming and/or tingling sensate. Such compositions may enhance or reduce the impact of the sensate, such as by dilution, or may attenuate or otherwise alter the properties or perception of the sensate, due to antagonistic or synergistic effects between the components of the compositions. Sensates are useful to impart cooling, warming, and/or tingling sensations to the skin or to mucous membranes of the oral cavity or pharynx. As such, sensates may be useful as flavors or fragrances in a wide range of compositions and products. Compositions such as these may provide an immediate warming, cooling, and or tingling sensation upon application of the composition to the body. In some embodiments, this helps provide an emollient effect. In some embodiments, the compounds of the present disclosure (e.g., Compound 1 or any of 1.1-1.62) or the compositions of the present disclosure (e.g., Composition 2 or any of 2.1-2.22) may also serve as one or more of a viscosity adjusting agent, a carrier, a distributing agent, a diluent agent, or a retention agent, for the sensate in the composition. This may help result in a sensate composition which imparts a controlled, sustained and/or delayed cooling, warming or tingling sensation.

In some embodiments of the above aspect, the sensate interacts with the TRPV protein in order to induce or reduce the desired cooling or warming effect. In some embodiments of the above aspect, the sensate is a natural compound, and in other embodiments the sensate is a synthetic compound.

Suitable cooling sensates include: menthol, levomenthol, peppermint oil, n-N-substituted-p-menthane-3-carboxamides, acyclic tertiary and secondary carboxamides, 3-1-menthoxy propane-1,2-diol, and mixtures thereof.

Suitable warming sensates include: vanillyl n-butyl ether, vanillyl alcohol n-propyl ether, vanillyl alcohol isopropyl ether, vanillyl alcohol isobutyl ether, vanillyl alcohol n-amino ether, vanillyl alcohol isoamyl ether, vanillyl alcohol n-hexyl ether, vanillyl alcohol methyl ether, vanillyl alcohol ethyl ether, gingerol, shogaol, paradol, zingerone, capsaicin, dihydrocapsaicin, nordihydrocapsaicin, homocapsaicin, homodihydrocapsaicin, ethanol, isopropyl alcohol, isoamyl alcohol, benzyl alcohol, eugenol, cinnamon oil, cinnamic aldehyde and phosphate derivatives thereof, pine needle oil, wintergreen oil, rosemary oil, eucalyptus oil, incense oil, and mixtures thereof. In some embodiments, the cooling sensate is combined with a metal ion (e.g., stannous, calcium, zinc, copper and the like) or a non-metal counter ion (e.g., fluoride and the like) to provide enhanced activity of a coolant in term of onset, intensity, or impact and duration.

Suitable tingling sensates include Jambu oleoresin extract, particularly for use in food products.

In some embodiments, a sensate is used to induce a revulsive effect, particularly in topical compositions. Suitable sensates for this purpose include menthol, pine needle oil, orange oil, lemon oil, wintergreen oil, bergamot oil, rosemary oil, lavender oil, glycosaminoglycans, and mixtures thereof.

In some embodiments, the sensate is a chemesthetic compound, which is a compound which induces trigeminal sensation.

Product compositions according to the present disclosure comprising such sensates include: cosmetics (such as lipstick, after shave lotions, foundations and the like), personal care products (such as skin creams, astringent lotions, cleansing lotions, deodorants, shampoos, conditioners, soaps, hair gels, hair tonics, hair growth stimulants, shaving foams, shaving creams, bubbling bath beads, insect repellent sprays, and the like) and pharmaceuticals products (such as, analgesic preparations, lozenges and the like).

Other suitable additives include: flavorants (e.g., berry flavors such as pomegranate, acai, raspberry, blueberry, strawberry, boysenberry, and/or cranberry; natural or synthetic flavors or aromas, such as peppermint, spearmint, wintergreen, chocolate, licorice, citrus; fruit flavors, such as apple, peach, pear, cherry, plum, orange, lime, grape, mango, passion fruit, pineapple, and grapefruit, gamma octalactone, vanillin, ethyl vanilline, butter, rum, coconut, almond, pecan, walnut, hazelnut, French vanilla, sugar cane, maple, cassis, caramel, banana, malt, espresso, white chocolate, spice flavors such as cinnamon, clove, cilantro, basil, oregano, garlic, mustard, nutmeg, rosemary, thyme, tarragon, dill, sage, anise, and fennel, methyl salicylate, linalool, jasmine, coffee, olive oil, sesame oil, sunflower oil, bergamot oil, geranium oil, peanut oil, lemon oil, ginger oil, balsamic vinegar, rice wine vinegar, red wine vinegar; vegetable flavors, such as tomato, carrot, spinach, broccoli, squash, onion, beet, turnip, parsnip, asparagus, pepper, fennel, zucchini, potato; and any combinations thereof); supplemental vitamins (e.g., vitamin A, vitamin D, vitamin E, vitamin K, thiamine, riboflavin, niacin, folic acid, pyridoxin, choline, inositol, vitamin B12, PABA, vitamin C, and mixtures thereof); preservatives (e.g., methyl paraben, propyl paraben, sodium propionate, citric acid, ascorbic acids, sorbic acid alkali metal salts, such as potassium sorbate, benzoic acid alkali metal salts, such as sodium benzoate, and the like); nutraceuticals (e.g., compounds derived from natural food sources and/or genetically modified food sources); and amino acids (e.g., valine, leucine, isoleucine, lysine, threonine, tryptophan, methionine, and phenylalanine, alanine, arginine, asparagine, aspartic acid, cysteine, glutamic acid, glutamine, glycine, histidine, proline, serine, tyrosine and mixtures thereof). Another particularly useful additive is arrowroot powder, which can be used as a substitute for talc, such as in cosmetic compositions.

In other embodiments of the preceding aspects, especially the fourth aspect, the present disclosure provides a composition comprising Compound 1 or any of 1.1-1.62, or a Composition 2 or any of 2.1-2.22, or any mixtures thereof, or Product 1 or any of 1.1-1.47, optionally wherein the composition or product further comprises one or more additives, as described hereinabove, wherein the composition or product is packaged in a container or device comprising packaging made from high density polyethylene (HDPE), low density polyethylene (LDPE), polypropylene (PP) or polyethylene terephthalate (PET), or a combination thereof. Preferably, the composition or product is packaged in a container or device comprising packaging made from high density polyethylene (HDPE). In further embodiments, the present disclosure provides:

4.1 A composition comprising a composition comprising
    Compound 1 or any of 1.1-1.62, or a Composition 2 or any of 2.1-2.22, or any mixtures thereof, or Product 1 or any of 1.1-1.47, optionally wherein the composition or product further comprises one or more additives, as described hereinabove, wherein the composition or product is packaged in a container or device comprising packaging made from high density polyethylene (HDPE), low density polyethylene (LDPE), polypropylene (PP) or polyethylene terephthalate (PET), or a combination thereof.

4.2 Composition or product 4.1, wherein the packaging comprises or consists of HDPE.

4.3 Composition or product 4.1 or 4.2, wherein the composition or product is a fragrance composition, perfume, soap, insect repellant and insecticide, detergent, household cleaning agent, air freshener, room spray, pomander, candle, cosmetic, toilet water, pre- and aftershave lotion, talcum powder, hair-care product, body deodorant, anti-perspirant, shampoo, skin care applications, pharmaceuticals, antimicrobials, pet litter, crop care formulation, or oil field, fracking or enhanced oil recovery formation.

4.4 Composition or product 4.3, wherein the composition or product is a cosmetic composition or a cosmetic product.

4.5 The composition or product according to 4.4, wherein the composition or product comprises a cosmetic preparation which is in the form of an emulsion.

4.6 The composition or product according to 4.5, wherein the emulsion is an oil-in-water emulsion (o/w emulsion).

4.7 The composition or product according to 4.5, wherein the emulsion is a water-in-oil emulsion (w/o emulsion).

4.8 The composition or product according to 4.7, 4.8 or 4.9, wherein the cosmetic preparation comprises the Compound 1 or any of 1.1-1.62 or the Composition 2 or any of 2.1-2.22 in an amount of 0.1 to 10% by weight based on the weight of the cosmetic preparation.

4.9 The composition or product according to any one of 4.4 to 4.10, wherein the composition or product comprises the Compound 1 or any of 1.1-1.62 or the Composition 2 or any of 2.1-2.22 in an amount of 0.1 to 10% by weight based on the weight of the cosmetic composition or product.

In a fifth aspect the, the present disclosure provides a method of using a Compound 1 or any of 1.1-1.62, or a Composition 2 or any of 2.1-2.22, or any mixtures thereof, in the manufacture of a Product Composition (e.g., Product Composition 1, et seq.), or Composition or Product 4.1-4.9, for example, a fragrance composition, perfume, soap, insect repellant and insecticide, detergent, household cleaning agent, air freshener, room spray, pomander, candle, cosmetic, toilet water, pre- and aftershave lotion, talcum powder, hair-care product, body deodorant, anti-perspirant, shampoo, skin care applications, pharmaceuticals, antimicrobials, pet litter, crop care formulation, or oil field, fracking or enhanced oil recovery formation).

An added benefit of these materials described herein is that they are expected to be fully biodegradable and biocompatible.

During the course of the evaluation of these polyethers, it was surprisingly observed that the depolymerization back to monomer would spontaneously occur at ~180° C. for the citronellol-type polymers. This thermal depolymerization property, or similar enzymatic and/or, acid catalyzed depolymerization properties could be beneficially used to deliver citronellol monomer in a controlled fashion over time.

In one aspect, thermal depolymerization could be used to deliver monomer into the air in a controlled release. In one aspect, the invention contemplates using the compounds of Compound 1, et seq., and/or Composition 2, et seq., e.g., as produced by Method 3, et seq., e.g., in candles or thermal dispensers used for odor control and/or mosquito control, in low pH industrial cleaners which could have the depolymerized monomer ingredient released over time to promote beneficial odor, and laundry detergents that could use enzymes to digest the polymers over time to have fresh odor over longer periods.

Other aspects regarding the use of compounds and compositions of the present disclosure may be found as disclosed in US2017/0283553 and WO2019/028053, the contents of which are incorporated by reference herein in their entireties The details of one or more embodiments of the invention are set forth in the accompanying description below. Unless defined otherwise, all technical and scientific terms used herein have the same meaning as commonly understood by one of ordinary skill in the art to which this invention belongs. In the case of conflict, the present specification will control.

Unless otherwise indicated, it is to be understood that the terminology used herein is for the purpose of describing particular embodiments only and is not intended to be limiting. In this specification and in the claims that follow, reference will be made to a number of terms, which shall be defined to have the definitions set forth below.

As used herein, the singular forms "a," "an," and "the" include plural referents unless the context clearly dictates otherwise. Thus, for example, reference to "a reactant" includes not only a single reactant but also a combination or mixture of two or more different reactant, reference to "a substituent" includes a single substituent as well as two or more substituents, and the like.

As used herein, the phrases "for example," "for instance," "such as," or "including" are meant to introduce examples that further clarify more general subject matter. These examples are provided only as an aid for understanding the disclosure, and are not meant to be limiting in any fashion. Furthermore, as used herein, the terms "may," "optional," "optionally," or "may optionally" mean that the subsequently described circumstance may or may not occur, so that the description includes instances where the circumstance occurs and instances where it does not. For example, the phrase "optionally present" means that an object may or may not be present, and, thus, the description includes instances wherein the object is present and instances wherein the object is not present.

As used herein, the phrase "having the formula" or "having the structure" is not intended to be limiting and is used in the same way that the term "comprising" is commonly used.

In some formulae of the present application, one or more chiral centers are identified by an asterisk placed next to the chiral carbon. In other formulae, no chiral center is identified, but the chiral isomers are nonetheless covered by these formulae.

Some compounds of the present invention can exist in a tautomeric form which is also intended to be encompassed within the scope of the present invention.

"Tautomers" refers to compounds whose structures differ markedly in arrangement of atoms, but which exist in easy and rapid equilibrium. It is to be understood that the compounds of the invention may be depicted as different tautomers. it should also be understood that when compounds have tautomeric forms, ail tautomeric forms are intended to be within the scope of the invention, and the naming of the compounds does not exclude any tautomeric form. Further, even though one tautomer may be described, the present invention includes all tautomers of the present compounds.

As used herein, the term "salt" can include acid addition salts including hydrochlorides, hydrobromides, phosphates, sulfates, hydrogen sulfates, alkylsulfonates, arylsulfonates, acetates, benzoates, citrates, maleates, fumarates, succinates, lactates, and tartrates; alkali metal cations such as $Na^+$, $K^+$, Li+, alkali earth metal salts such as $Mg^{2+}$ or $Ca^{2+}$, or organic amine salts, or organic phosphonium salts.

The term "alkyl" as used herein refers to a monovalent or bivalent, branched or unbranched saturated hydrocarbon group having from 1 to 22 carbon atoms, typically although, not necessarily, containing 1 to about 12 carbon atoms, such as methyl, ethyl, n-propyl, isopropyl, n-butyl, isobutyl, t-butyl, octyl, and the like. It will be understood from the context that in some cases the term "alkyl" refers to a bivalent radical rather than a monovalent radical. In such cases where the context indicated that the radical is bivalent, while the term "alkyl" may be further exemplified as "methyl," "ethyl," "propyl," etc., as a bivalent radical such terms would be understood as referring to "—$CH_2$—", "—$CH_2CH_2$—" and "—$CH_2CH_2CH_2$—", respectively.

The term "alkenyl" as used herein refers to a monovalent or bivalent, branched or unbranched, unsaturated hydrocarbon group typically although not necessarily containing 2 to about 12 carbon atoms and 1-10 carbon-carbon double bonds, such as ethylene, n-propylene, isopropylene, n-butylene, isobutylene, t-butylene, octylene, and the like.

The term "alkynyl" as used herein refers to a monovalent or bivalent, branched or unbranched, unsaturated hydrocarbon group typically although not necessarily containing 2 to about 12 carbon atoms and 1-8 carbon-carbon triple bonds, such as ethyne, propyne, butyne, pentyne, hexyne, heptyne, octyne, and the like.

The term "aryl" as used herein refers to an aromatic hydrocarbon moiety comprising at least one aromatic ring of 5-6 carbon atoms, including, for example, an aromatic hydrocarbon having two fused rings and 10 carbon atoms (i.e, naphthalene).

By "substituted" as in "substituted alkyl," "substituted alkenyl," "substituted alkynyl," and the like, it is meant that in the alkyl, alkenyl, alkynyl, or other moiety, at least one hydrogen atom bound to a carbon atom is replaced with one or more non-hydrogen substituents, e.g., by a functional group.

The terms "branched" and "linear" (or "unbranched") when used in reference to, for example, an alkyl moiety of $C_a$ to $C_b$ carbon atoms, applies to those carbon atoms defining the alkyl moiety. For example, for a $C_4$ alkyl moiety, a branched embodiment thereof would include an isobutyl, whereas an unbranched embodiment thereof would be an n-butyl. However, an isobutyl would also qualify as a linear $C_3$ alkyl moiety (a propyl) itself substituted by a $C_1$ alkyl (a methyl).

Examples of functional groups include, without limitation: halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), mono-substituted $C_1$-$C_{24}$ alkylcarbamoyl (—(CO)—NH($C_1$-$C_{24}$ alkyl)), di-substituted alkylcarbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—N$^+$≡C$^-$), cyanato (—O—C≡N), isocyanato (—O—N$^+$≡C—), isothiocyanato (—S—C≡N), azido (—N=N$^+$=N$^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_5$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{20}$ alkaryl, $C_6$-$C_{20}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O$^-$)$_2$), phosphinato (—P(O)(O—)), phospho (—$PO_2$), phosphino (—$PH_2$), mono- and di-($C_1$-$C_{24}$ alkyl)-substituted phosphino, mono- and di-($C_5$-$C_{20}$ aryl)-substituted phosphino; and the hydrocarbyl moieties such as $C_1$-$C_{24}$ alkyl (including $C_1$-$C_{18}$ alkyl, further including $C_1$-$C_{12}$ alkyl, and further including $C_1$-$C_6$ alkyl), $C_2$-$C_{24}$ alkenyl (including $C_2$-$C_{18}$ alkenyl, further including $C_2$-$C_{12}$ alkenyl, and further including $C_2$-$C_6$ alkenyl), $C_2$-$C_{24}$ alkynyl (including $C_2$-$C_{18}$ alkynyl, further including $C_2$-$C_{12}$ alkynyl, and further including $C_2$-$C_6$ alkynyl), $C_5$-$C_{30}$ aryl (including $C_5$-$C_{20}$ aryl, and further including $C_5$-$C_{12}$ aryl), and $C_6$-$C_{30}$ aralkyl (including $C_6$-$C_{20}$ aralkyl, and further including $C_6$-$C_{12}$ aralkyl). In addition, the aforementioned functional groups may, if a particular group permits, be further substituted with one or more additional functional groups or with one or more hydrocarbyl moieties such as those specifically enumerated above. For example, the alkyl or alkenyl group may be branched. For example, the "substituent" is an alkyl group, e.g., a methyl group.

As used herein, the term "fragrance composition" means a mixture of fragrance ingredients, e.g., including the Compound 1 or any of 1.1-1.62, or a Composition 2 or any of 2.1-2.22, including auxiliary substances if desired, dissolved in a suitable solvent or mixed with a powdery substrate used to provide a desired odor to a product, optionally packaged according to Composition of Product 4 or 4.1-4.9.

Fragrance and ingredients and mixtures of fragrance ingredients that may be used in combination with the disclosed compound for the manufacture of fragrance compositions include, but are not limited to, natural products including extracts, animal products and essential oils, absolutes, resinoids, resins, and concretes, and synthetic fragrance materials which include, but are not limited to, alcohols, aldehydes, ketones, ethers, acids, esters, acetals, phenols, ethers, lactones, furansketals, nitriles, acids, and hydrocarbons, including both saturated and unsaturated compounds and aliphatic carbocyclic and heterocyclic compounds, and animal products.

As used herein, "citronellol polymer" and "prenol polymer" is meant to include all derivatives and cyclic forms of the citronellol and prenol and polymer.

In the present specification, the structural formula of the compounds represents a certain isomer for convenience in some cases, but the present invention includes all isomers, such as geometrical isomers, optical isomers based on an asymmetrical carbon, stereoisomers, tautomers, and the like. In addition, a crystal polymorphism may be present for the compounds represented by the formula, it is noted that any crystal form, crystal form mixture, or anhydride or hydrate thereof is included in the scope of the present invention.

Where a range is recited, such as 0-10 or 1-7, the range embraces all integer values within the range, as well as integer subranges. Thus, the range 0-10 includes 0-9, 0-8, 0-7, 0-6, 0-5, 0-4, 0-3, 0-2, 1-10, 1-9, 1-8, 1-7, 1-6, 1-5, 1-4, 1-3, 1-2, 1-9, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 4-4, 4-3, 5-10, 5-9, 5-8, 5-7, 5-6, 6-10, 6-9, 6-8, 6-7, 7-10, 7-9, 7-8, 8-10, 8-9, 9-10, 0, 1, 2, 3, 4, 5, 6, 7, 8, 9 and 10.

All percentages used herein, unless otherwise indicated, are by volume.

All ratios used herein, unless otherwise indicated, are by molarity.

EXAMPLES

Example 1: Continuous Citronellol Polymerization Over Cation Exchange Resin

A 6-foot-long, 0.25-inch smooth bore stainless steel tube with a 0.01-inch wall thickness is packed with Amberlyst resin and is coiled and outfitted with PTFE tubing on either end for continuous flow. The coil is heated to 50° C. in an oil bath and 300 g of citronellol is pumped through the packed coil at a rate of 2 ml/min. The material coming out of the coil has reached a high degree of polymerization as shown by $^1$H-NMR analysis. NMR indicates a dramatic increase in the number of protons associated with methylene groups adjacent to ether oxygen atoms (~3.3 ppm) compared to the protons associated with methylene groups adjacent to alcohol oxygen atoms (~3.6 ppm). The integrated ratio is found to be about 1:1 for these two different sets of protons.

Pressurized nitrogen gas is used to expel all material from the coil. The collected material is further distilled under vacuum (0.7 mbar) at elevated temperature (up to 160° C.) to remove monomeric and dimeric species, resulting in a clear, odorless liquid identified as follows:

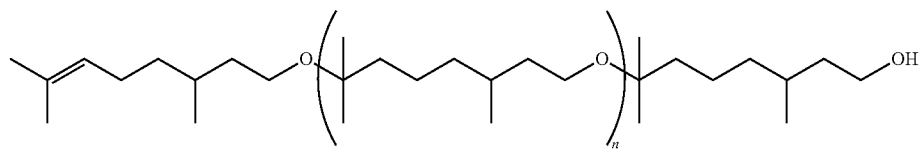

Various fractions may be collected, each having different values for number average molecular weight, weight average molecular weight, polydispersity and values of n. Such fractions have differing physical properties, such as viscosity, refractive index, boiling point, and surface tension.

One fraction is obtained wherein the citronellol polymer has an average value of n of 0-4. Another fraction is obtained wherein the citronellol polymer has an average value of n of 1-7.

Example 2: Polycitronellol-Limonene Oxide Product

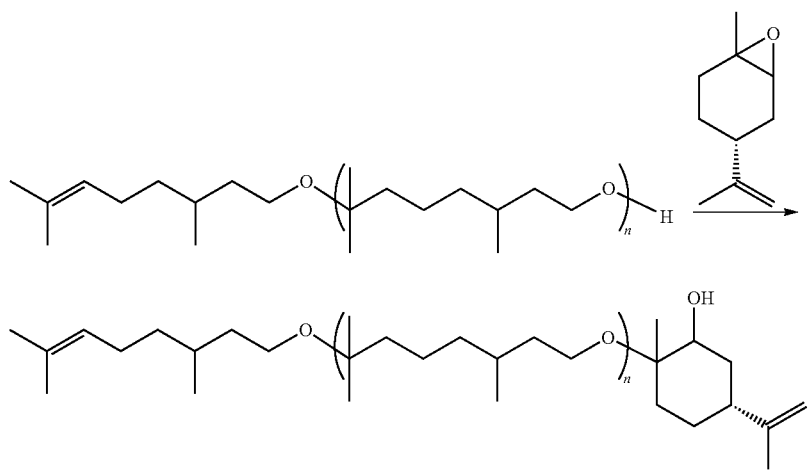

A mixture of polycitronellol (141 g) and limonene oxide (34.4 g, 0.75 eq.) is treated with Amberlyst resin (5%, 7 g) and allowed to stir at room temperature for two hours. The reaction is monitored by thin-layer chromatography (TLC) and $^1$H NMR during the process. No change compared to the starting materials is noted. The reaction is then heated to 40° C. for an additional two hours. Product is evident in the mixture, but the reaction is incomplete. The reaction is heated at 45° C. for additional four hours. TLC and NMR showed the consumption of starting material (see FIG. 1). The reaction mixture is filtered through Celite to remove the resin. 70 g of reaction mixture is collected. The mixture is distilled at elevated temperature and reduced pressure (temperature 123.5° C. through 132.3° C., pressure 2.43 mbar through 2.51 mbar). The product thus obtained was characterized by NMR and is consistent with the desired product.

Example 3: Determination of Polydispersity of Citronellol Polymer Derivatives

A sample of a citronellol polymer derivative is weighed out (e.g., 20-25 mg in a 10-mL volumetric flask) and diluted with solvent (e.g., THF, unstabilized) to flask volume. The mixture is shaken well until it is homogenous. An isocratic chromatographic condition is used to separate the polymer peaks for analysis. The chromatographic parameters are listed below:
Column: Agilent Oligopore GPC, 6 μm, 3.5 mm×700 mm
Diluent: THF, without BHT inhibitor (unstabilized)
Mobile Phase: THF, without BHT inhibitor (unstabilized)
Flow Rate: 1.0 mL/min
Column Temperature: 25±2° C.
Detection: 220 nm
Injection Volume: 30 μL
Run Time: 25 minutes
Calculation: Because there is the one double bond in each polymer molecule is the only functional group absorbing light at a 220 nm wavelength, the area % values derived from the chromatogram are equivalent to mole % values. Therefore, the HPLC data report values for peak are used for calculation, and only need to be corrected for weight percent calculation.
Mass=(theoretical molecular weight)×(Area %)
Mass %=(mass/sum of mass)×100
Mn (number average)=Area in mAUs/molecular weight
Mw (weight average)=(Area in mAUs)×(molecular weight)
PDI (polydispersity index)=Mw/Mn
From the HPLC chromatogram, each peak can be characterized by its retention time, % Area, and molecular weight. From these values, mass and mass % may be derived. Number average molecular weight, weight average molecular weight, and polydispersity are then calculated from these FIGURES.

Various citronellol polymers and citronellol polymer derivatives are tested for polydispersity according to this procedure. For one polymer, the data shows that the primary component of the citronellol polymer derivative composition is the dimer, present in an estimated amount of 50 weight percent. The remaining major components are trimer, tetramer, pentamer and hexamer, whose total amount is estimated at 50.36 weight percent. For another polymer, the data shows that the primary component of the citronellol polymer composition is the trimer, present in an estimated amount of about 45-57 weight percent. The remaining major components are the tetramer, pentamer, and hexamer, whose total amount is estimated at 42-46 weight percent, with the balance dimer, heptamer and octamer.

The invention claimed is:
1. A compound according to Formula I below:

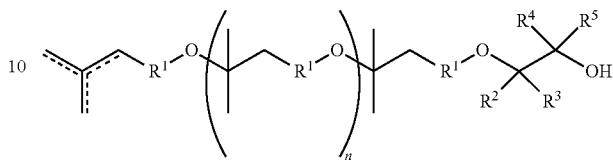

wherein $R^1$ is optionally substituted $C_1$-$C_{12}$ alkyl;
$R^2$, $R^3$, $R^4$, and $R^5$ are each independently hydrogen, optionally substituted $C_1$-$C_{12}$ alkyl, optionally substituted $C_2$-$C_{12}$ alkenyl, optionally substituted $C_2$-$C_{12}$ alkynyl, optionally substituted aryl, or
$R^2$ and $R^3$, $R^4$ and $R^5$, or $R^3$ and $R^5$, are taken together to form an optionally substituted $C_3$-$C_{12}$ cycloalkyl or optionally substituted $C_3$-$C_{12}$ cycloalkenyl; and
n is an integer between 0 and 20;
wherein ═══ represents either a single bond or double bond.

2. The compound according to claim 1, wherein $R^1$ is optionally substituted linear $C_1$-$C_{12}$ alkyl or optionally substituted branched $C_1$-$C_{12}$ alkyl.

3. The compound according to claim 1, wherein $R^1$ is unsubstituted linear $C_1$-$C_{12}$ alkyl or unsubstituted branched $C_3$-$C_{12}$ alkyl.

4. The compound according to claim 1, wherein $R^1$ is $CH_2CH_2CH(CH_3)CH_2CH_2$.

5. The compound according to claim 1, wherein one or more of $R^2$, $R^3$, $R^4$, and $R^5$ are each independently hydrogen.

6. The compound according to claim 1, wherein one or more of $R^2$, $R^3$, $R^4$, and $R^5$ are each independently unsubstituted $C_{1-12}$ alkyl.

7. The compound according to claim 1, wherein one or more of $R^2$, $R^3$, $R^4$, and $R^5$ are each independently substituted $C_{1-12}$ alkyl.

8. The compound according to claim 1, wherein $R^2$ and $R^4$ are each independently hydrogen or unsubstituted $C_{1-6}$ alkyl and $R^3$ and $R^5$ are taken together to form an optionally substituted $C_3$-$C_{12}$ cycloalkyl or optionally substituted $C_3$-$C_{12}$ cycloalkenyl.

9. The compound according to claim 1, wherein n is 0, 1, 2, 3, or 4.

10. The compound according to claim 1, wherein the terminal group

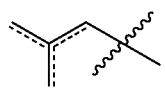

is

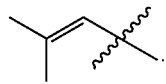.

11. A compound selected from the group consisting of:
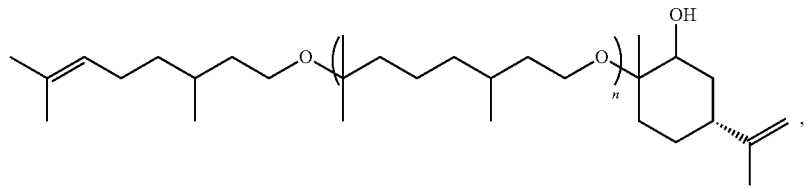
wherein n is 0-20;
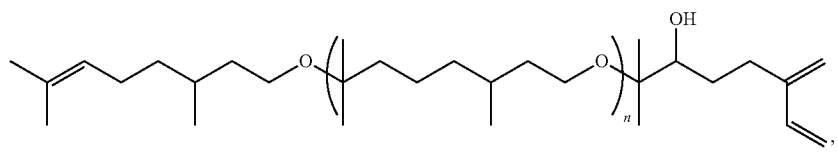
wherein n is 0-20;
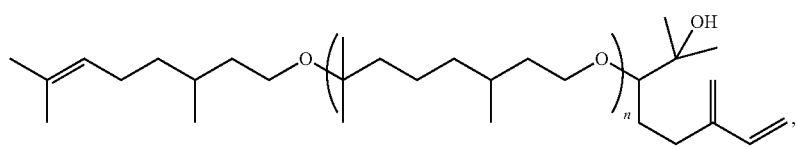
wherein n is 0-20;
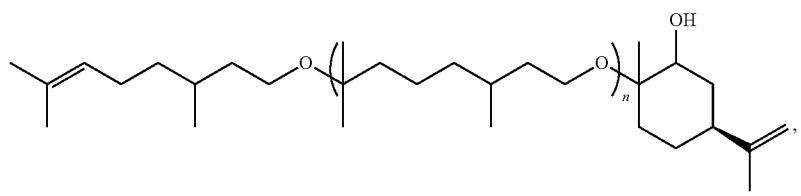
wherein n is 0-20;
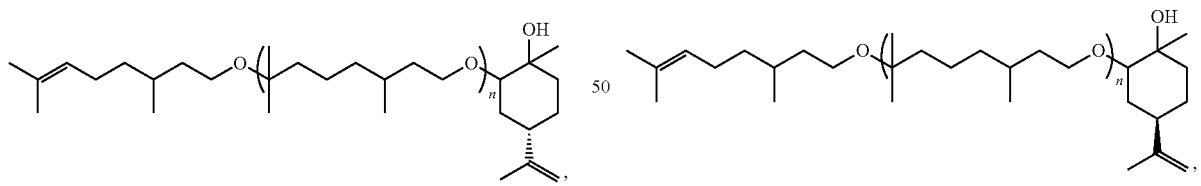
wherein n is 0-20;   wherein n is 0-20;
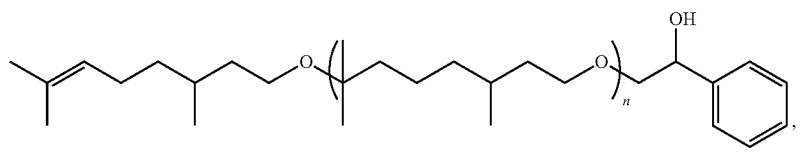
wherein n is 0-20;

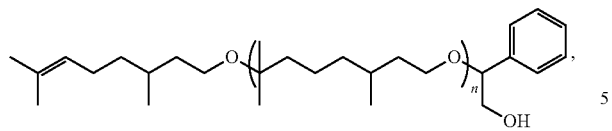
wherein n is 0-20;
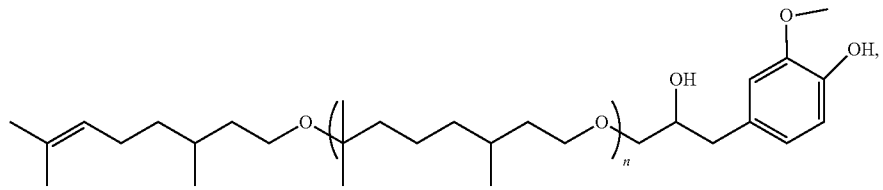
wherein n is 0-20;
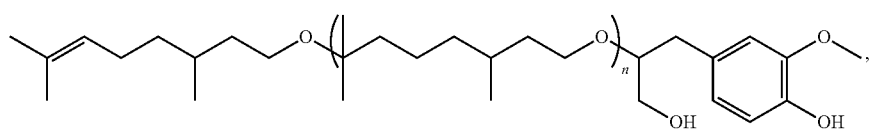
wherein n is 0-20;
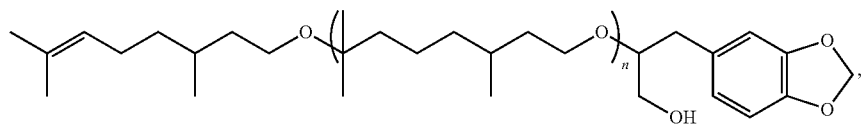
wherein n is 0-20;
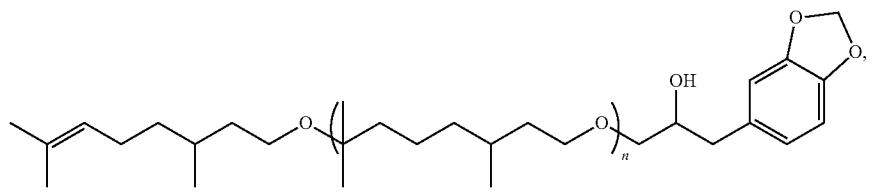
wherein n is 0-20;
wherein n is 0-20;
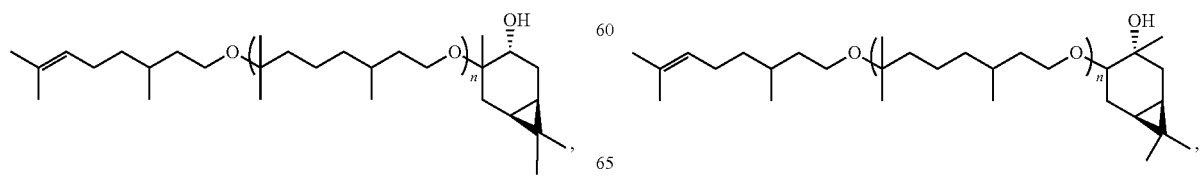
wherein n is 0-20;

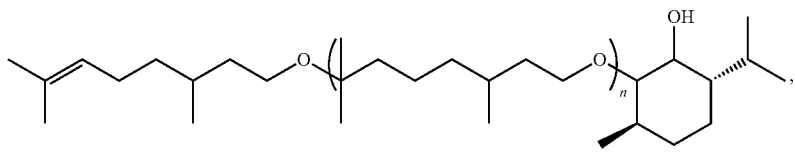

wherein n is 0-20;

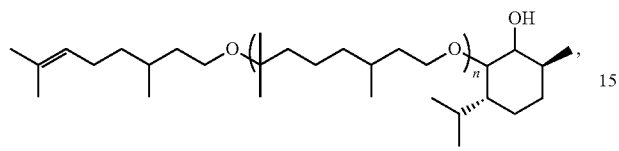

wherein n is 0-20;

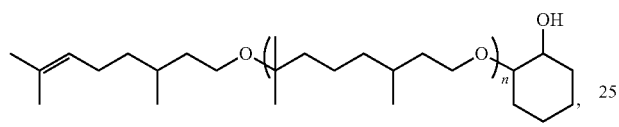

wherein n is 0-20;

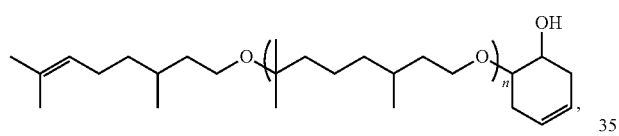

wherein n is 0-20;

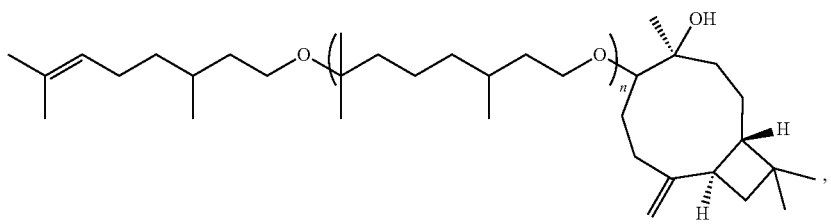

wherein n is 0-20; and

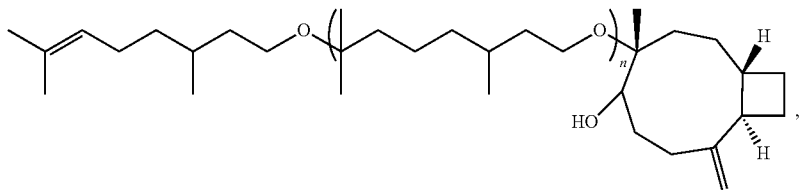

wherein n is 0-20.

12. A composition comprising the compound of Formula I according to claim 1.

13. The composition according to claim 12, wherein the composition comprises said Compound of Formula I wherein n is 0 to an extent of greater than 40%, said percent being measured either as the number percent of the molecules in the composition or as the weight percent of the total weight of the composition.

14. The composition according to claim 12, wherein the composition comprises one or more Compounds of Formula I wherein each compound independently has a value of n from 0 to 4, and each compound being present in an amount of at least 5 to 50% said percent being measured either as the number percent of the molecules in the composition or as the weight percent of the total weight of the composition.

15. The composition according to claim 12, wherein the composition comprises more than one Compound of Formula I, wherein the compounds of Formula I in the composition have an average n value of about 0, measured either as a weight average or number average, optionally about 0.5.

16. A method of making the compound according to claim 1, wherein $R^1$ is $CH_2CH_2CH(CH_3)CH_2CH_2$,

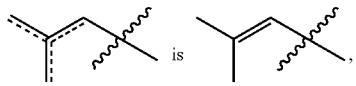

and n is an integer from 0-20 comprising the step of reacting a compound of Formula I(a):

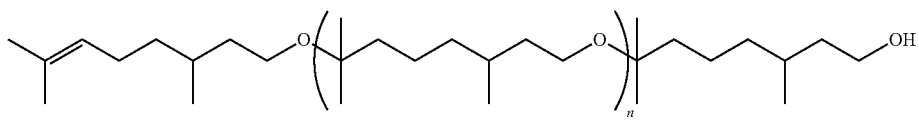

wherein n is 0-20;
with a compound of Formula A:

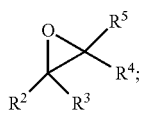

wherein $R^2$, $R^3$, $R^4$, and $R^5$ are as defined in claim 1; in the presence of an acid or base catalyst, followed by isolation and complete or partial purification of the compound of Formula I.

17. A product composition which product composition comprises a compound according to claim 1.

18. The product composition according to claim 17, wherein the product is selected from a fragrance product, perfume product, soap product, insect repellant product, insecticide product, detergent product, household cleaning agent product, air freshener product, room spray product, pomander product, candle product, cosmetic product, toilet water product, lotion product, talcum powder product, haircare product, body deodorant product, anti-perspirant product, shampoo product, pet litter product, topically applied skin care product, paint or coating product, lubricant product, plastic product, defoamer product, hydraulic fluid product, antimicrobial product, crop care product, a product for enhanced oil recovery, fracking and/or other oil field applications, a nail polish remover product, writing ink or printing ink product, an adhesive product, an oral care product, a food product, or a pharmaceutical product.

19. The product composition according to claim 18, wherein the composition further comprises one or more additives selected from: a cooling sensate, a warming sensate and/or a tingling sensate; a flavorant or fragrance; vitamins, minerals, nutraceuticals, energizing agents, soothing agents, coloring agents, amino acids antioxidants, preservatives, pH modifying agents, viscosity adjusting agents, and combinations of any preceding.

20. The compound according to claim 1, wherein $R^1$ is $CH_2CH_2CH(CH_3)CH_2CH_2$,

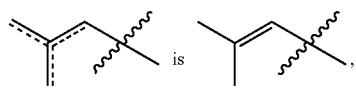

and n is an integer from 0-20.

* * * * *

UNITED STATES PATENT AND TRADEMARK OFFICE
CERTIFICATE OF CORRECTION

| | |
|---|---|
| PATENT NO. | : 11,820,865 B2 |
| APPLICATION NO. | : 17/758855 |
| DATED | : November 21, 2023 |
| INVENTOR(S) | : Patrick Foley et al. |

It is certified that error appears in the above-identified patent and that said Letters Patent is hereby corrected as shown below:

In the Specification

Column 5, from Line 25 to the bottom of the Column:

" 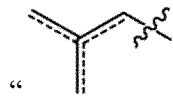

1.36 Compound 1 or any of 1.1 *et seq.*, wherein the terminal group is

 ."

Should be changed to:
"1.36 Compound 1 or any of 1.1 *et seq.*, wherein the terminal group

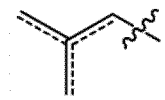

is

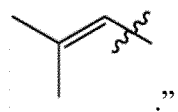 ."

Signed and Sealed this
Thirtieth Day of January, 2024

Katherine Kelly Vidal
*Director of the United States Patent and Trademark Office*